United States Patent [19]

Heyman et al.

[11] Patent Number: 5,087,251
[45] Date of Patent: Feb. 11, 1992

[54] ENTIRELY DISPOSABLE UNITARY URINE DRAINING BAG AND SUPPORT HARNESS SYSTEM

[76] Inventors: Arnold M. Heyman, 2701 W. Alameda Ave., Burbank, Calif. 91505; Paul Choksi, 10935 Yolanda Ave., Northridge, Calif. 91326

[21] Appl. No.: 639,328

[22] Filed: Jan. 9, 1991

Related U.S. Application Data

[63] Continuation of Ser. No. 317,042, Feb. 28, 1989, abandoned, which is a continuation of Ser. No. 127,519, Dec. 1, 1987, abandoned, which is a continuation of Ser. No. 900,818, Jul. 28, 1986, abandoned.

[51] Int. Cl.$^5$ .......................... A61M 1/00; A61F 5/44
[52] U.S. Cl. ................................. 604/327; 604/329; 604/331
[58] Field of Search ..................... 604/322-327, 604/331; 128/760, 767

[56] References Cited

U.S. PATENT DOCUMENTS

| | | | |
|---|---|---|---|
| 2,883,985 | 4/1959 | Evans | 604/327 |
| 3,186,409 | 1/1965 | Barte | 604/322 |
| 3,228,444 | 1/1966 | Weber et al. | 128/767 |
| 3,371,897 | 3/1968 | Serany, Jr. et al. | 604/326 |
| 4,085,755 | 4/1978 | Burrage | 604/323 |
| 4,122,851 | 10/1978 | Grossner | 128/DIG. 15 |
| 4,153,189 | 5/1979 | Hughes | 2/DIG. 6 |
| 4,511,358 | 4/1985 | Johnson et al. | 604/327 |

FOREIGN PATENT DOCUMENTS

| | | | |
|---|---|---|---|
| 677593 | 1/1964 | Canada | 604/322 |
| 2106395 | 4/1983 | United Kingdom | 604/351 |

*Primary Examiner*—Ronald Frinks
*Assistant Examiner*—R. Clarke
*Attorney, Agent, or Firm*—Spensley, Horn, Jubas & Lubitz

[57] ABSTRACT

A one wall of a plastic urine bag is extended as a broad sheet terminating in a rolled-over belt loop. The belt loop is threaded by a fabric belt, which is secured about a patient's waist, permitting the urine bag to hang in the area of the patient's leg. The fabric belt has Velcro ® "loops" entirely upon its surface and is fastened by a tab of Velcro ® "hooks". The catheter is taped to the broad sheet. A lower port of the urine bag has a valve for gravity drainage of collected fluids. The unitary urine bag and support harness in combination with the belt is low cost, sanitary, comfortable for patient use, easy of assembly, tamper resistant, and entirely disposable.

25 Claims, 1 Drawing Sheet

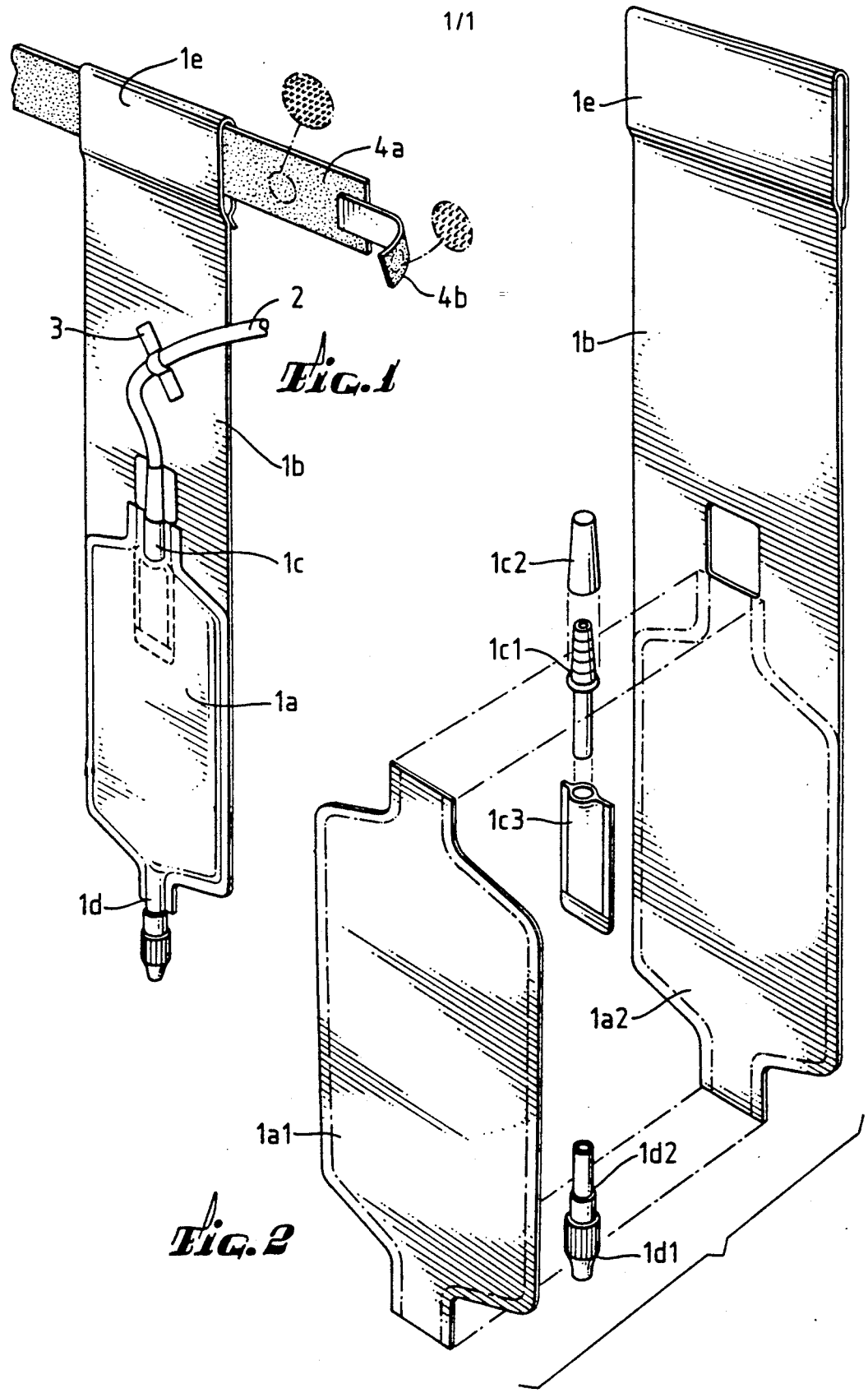

ENTIRELY DISPOSABLE UNITARY URINE DRAINING BAG AND SUPPORT HARNESS SYSTEM

This application is a continuation of my prior application Ser. No. 07/317,042 filed Feb. 28, 1989 now abandoned, which is a continuation of my prior application Ser. No. 07/127,519, filed Dec. 01, 1987 now abandoned, which is a continuation of application Ser. No. 06/900,818 filed July 28, 1986, now abandoned.

BACKGROUND OF THE INVENTION

1. Field of the Invention

The field of the invention is urine collecting bags portable on the body of a person. More specifically, the invention concerns a disposable urine collection bag and its associated support harness system.

2. Description of the Prior Art

People may sometimes be afflicted with urological diseases, maladies, and ailments impairing their ability to voluntarily control the evacuation or release of urine. This may also happen post-operatively because of anesthetic agents and drugs. Because of these problems a catheter may be inserted into the bladder for the collection of urine. Patients or persons suffering from incontinence may also be catheterized for the collection of urine. Patients who have been catheterized frequently wear, beneath their clothing or gown, urine collecting or drainage apparatus which allows collection and storage of the discharged urine.

Prior art urine collecting apparatus is generally marked by complexity, with separate components cooperating for the urine collecting and support harness functions. Early urine collecting apparatus employed a disposable plastic bag customarily clamped or held to the leg of a wearer by elastic latex bands tightly encircling the wearer's leg. These bands constricted the leg, tended to reduce blood circulation in the leg, and were uncomfortable to the wearer. The bands were prone to cause irritation of the skin by causing blisters and pulling body hair. Consequently, various harness systems for supporting a urine collection bag from the waist came to be developed.

U.S. Pat. No. 3,897,785 to Homer D. Barto, Jr. shows a harness support system for a disposible urine bag. The system has a separate, disposable, urine collection bag attached to a support sheet. The sheet is designed to hang from an adjustable belt positioned upon the wearer's waist when in use. The urine collection bag is supported upon the support sheet in the area of the patient's leg and communicates with the patient for receipt of urine through a catheter. Barto also shows leg bands designed to fit around the patient's leg in order to hold the support sheet, with the urine bag affixed thereto, to the leg.

U.S. Pat. No. 4,122,851 to Grossmer shows another belt-type carrier apparatus for urine bags. Within such apparatus downwardly hanging pouches support the urine bags. Grossmer additionally shows the use of a Velcro ® fastener for attaching a belt about the wearer's waist, and for attaching the pouches to the belt.

Resultantly from these separate urine bags and belt-type carrier apparatus in prior urine collection systems, it became necessary to make specialized accommodation to the positioning and holding of the catheter tube. Yet another patent addresses this concern. U.S. Pat. No. 4,096,863 teaches a locking device for holding a catheter tube in place, and for reducing irritation by eliminating the "floating effect" of the catheter tube. This locking device is used in the Dale ® Combo ® Catheter Tube Holder No. 0584-402 (announced in product sheet 925 dated July 1, 1978) of Bako Manufacturing Company, Inc., Plainville, Mass. 02762. The catheter (tube) and drainage bag with which the tube holder is used are not only not integral with the catheter tube holder, but are not even included in the packaged product as supplied.

The prior art systems for urine drainage and collection from a mobile patient generally show that the urine collection bag and the harness, or carrier, should be of separate, interactive, parts. Indeed, the patent of Barto is called a "HARNESS FOR A DISPOSABLE URINAL", and the patent of Grossmer is called a "CARRIER AND SKIN-PROTECTING COVER FOR URINE BAGS". This approach using separate system components is less than optimal for several reasons. Both urine bag and harness components must be carried within the inventory of the health care provider, and must be located and interoperatively assembled in order to initiate the service function upon the patient. If one part, the urine collection bag, is disposable while the remaining part, the harness, is not, then the harness, especially if it is cloth, is subject to becoming stained and contaminated during repeated usage. If such harness, often made of cloth or canvas, is attempted to be laundered and sanitized then it represents a small specialty item in laundering for which the labor costs of cleaning are likely to exceed the intrinsic worth.

The prior art urine collection systems comprised of separate constituent component bag and harness parts present scant obstacles to patient tampering and unauthorized disassembly of the system, such as by removing the urine bag from the support harness.

Finally, there are aesthetic concerns of which the patient is often accutely conscious. Although no urine collection system is likely to enhance the comfort or appearance of the human body, urine collection systems comprised of diverse parts have occasionally assumed an appearance which is arguably grotesque and outlandish. This especially includes systems which employ diverse metal brackets, holders, clamps, and the like—all toward the goal of positioning and retaining a considerable amount of paraphernalia on an ambulatory patient.

The present invention is directed to a simple, unified, integrated, low cost, aesthetically reasonable, effective, disposable and neat system of urine collection. It offers simplified aspects of construction and use. It offers improved sanitation. It also offers certain particular aspects of improved effective attachment to the patient's waist and improved effective support of the catherization tube which is in flow connection with the urine collection bag.

SUMMARY OF THE INVENTION

The present invention of an entirely disposable unitary urine drainage bag and support harness system is embodied in a unitary plastic urine collection bag and support sheet. A belt loop within the support sheet threads a belt. When in use, the belt is secured about the patient's waist by a Velcro ® fastening system. The unitary urine collection bag and support sheet hangs from the belt in a manner so that the collection bag is in the area near the patient's leg. The entry or top port of the collection bag communicates for the collection or drainage of urine or other fluids from the patient through a catheter. A bottom or drainage port with an integral valve or cap is used to empty the collection bag. The apparatus is entirely disposable, simple and economical of construction, comprised of a minimum number of pieces (two), resistent to patient tampering in the flow connection for collection of the urine, comfortable to wear, effectively and reliably secured, reasonably aesthetic, aseptic of construction, sanitary, and minimally subject to contamination during use. The apparatus exhibits ease of assembly, connection, operation, disconnection and disposal. Of all these attributes, simplicity and economy are paramount.

In the preferred embodiment implementation, the unitary urine collection bag and the plastic support sheet which forms a harness therefor are preferably entirely made from matt finish clear vinyl. The urine collection or drainage bag has a top port in flow connection with the urine (or other fluids) of the patient through a catheter. The top port is preferably flow connected through a low-cost unidirectional flow valve assuring that only ingress of urine to the collection bag is permitted.

The urine collection bag has a bottom port for being drained in the upright position. The bottom port preferably incorporates a twist-type low-cost valve or is sealed with a low-cost removable plastic cap.

The plastic support sheet serves as a harness. It provides a broad surface to which the catheter or other appliances may readily be secured by taping. The taping accords flexible and reliable positioning of the catheter, thereby increasing patient comfort. The plastic support sheet terminates in an integral belt loop which—due primarily to its breadth—is neither irritating to the patient, nor prone to cause buckling of the belt at the point of suspension of the unitary harness and urine drainage bag, nor prone to slide from its desired retention position upon the belt. The belt itself is preferably broad. It is preferably entirely formed of fabric coated over its entire surface with "loop" Velcro ®. The belt is affixed by a "hook" Velcro ® fastener which is a small generally rectangular, piece of Velcro stuck at one end of the belt. The belt is, correspondingly, readily adjustable to any size waist. Any excess belt length may be readily severed with scissors if found desirable. The belt is comfortable to wear, and reliable to support the unitary urine drainage bag and support harness.

The entire system of the invention is characterized by a simplicity and economy of construction. The system enables easy assembly and usage, reliable and sanitary function, and is readily disposable. The present invention is particularly intended to reduce problems occurring with ease of assembly, comfort in use, sanitation in use, ease of disassembly, and disposal or cleaning of components as compared to prior art systems.

BRIEF DESCRIPTION OF THE DRAWINGS

FIG. 1 shows an illustration of the present invention of an entirely disposable unitary urine drainage bag and support harness system disposed and connected as such would be in operational use.

FIG. 2 shows an exploded diagram of the construction of the unitary urine drainage bag and support harness.

DESCRIPTION OF THE PREFERRED EMBODIMENT

The present invention is embodied in an entirely disposable unitary urine drainage bag and support harness system. Equivalently to prior art urine drainage bags it provides a non-phlebitic comfort support that does not restrict venous flow. It may be used with indwelling urethral and external catheters as well as nephrostomy, ureterostomy, cystostomy and other types of catheters. No special significance should be attached to the words "drainage" or "collection", the urinary drainage bag of the present invention capturing liquid urine or other fluid delivered by tube, or catheter, howsoever such tube is otherwise connected. The invention provides an extended reservoir for ileal conduit devices. It may be connected to T-tube bileduct drainage, chest-tube drainage, or other drainage tubes.

The present invention of a unitary urine drainage bag and support harness system encourages dignified patient ambulation by shielding the urine specimen from view when worn in position under clothing or gown. Each apparatus is for single patient use, and is intended to be individually packaged. These and other characteristics establishing functional operability with reasonable accommodation to patient comfort and dignity are present to some degree in at least the more recent of prior art urine collection systems. Without sacrificing these fundamental characteristics the present invention will, however, be seen to offer unique attributes in economy and simplicity, ease of assembly, reliable and comfortable support in operation, sanitation, and disposability.

The present invention embodied in an entirely disposable unitary urine drainage bag and support harness system is shown positioned, and connected, as it would be in operational use in FIG. 1. The system contains a urine drainage bag, or reservoir, 1a which is integral with a support sheet 1b. Normally, as will be shown in FIG. 2, such support sheet 1b is formed of an extended wall, nominally the back wall disposed toward the patient, of the urine collection bag 1a. Alternatively, the urine collection bag may be separately formed, and then permanently affixed to plastic sheet 1b. Such affixation is, however, preferably not merely at selective points of attachment such as the corners of the urine collection bag 1a, but is instead over the entire area where such collection bag 1a and the plastic sheet 1b are in contact. Generally, the combination urine collection bag 1a and support sheet 1b presents a smooth, unified, continuous construction and appearance. The combination is basically a plastic urine collection bag with a much-elongated sidewall presenting a sheet extension behind the uppermost port of such urine collection bag.

Continuing in FIG. 1, the urine collection bag 1a has an uppermost port 1c and an lowermost port 1d. The uppermost port 1c is in flow connection with a tube catheter 2 which is plugged thereto. For secure positioning and support, the tube catheter 2 may be readily affixed to plastic sheet 1b with surgical tape 3. The catheter is thereby held at any desired position and orientation. The use of the surgical tape 3 to affix the catheter 2 to the urine collection system 1 solves a number of problems commonly encountered in the affixation of catheters. Problems with surface preparation and tape removal in taping to skin are eliminated because all connection is to the unitary urine drainage bag and support harness apparatus which is constructed of plastic. Meatal irritation occuring from meatal pressure points on the human body are eliminated because all connections are not directly to the patient, but rather to the urine drainage bag 1a and/or the support harness 1b. The method of affixing the catheter 2 by taping does not occlude the catheter or prevent its full and free conduct of the flow of urine. The taping method does not constrict the circulation of the patient with any "tourniquet effect". The catheter tape affixing method enables the desired position, orientation, and rigidity (immobility) of the catheter tube to be achieved. A variable extension in the length of the catheter as it further extends to connect to the patient is permitted.

Continuing in FIG. 1, the unitary urine drainage bag 1a and support belt 1b terminates in a roll-over belt loop 1e. This belt loop 1e is normally equally as broad as the support sheet 1b, and is sufficiently tall so as to thread a two-inch wide belt. The flap is normally rolled over from that side which is in contact with the waist of the patient outwards so that no seam can be felt by the torso of the patient. The preferred manner by which the belt loop is affixed is by compressive thermoplastic sealing in order to form a seam. The seam may also be formed by other methods known in the art of joining plastic sheet in order to produce a reliable and regular attachment.

The entire unitary urine drainage bag 1a, with plastic sheet extension 1b terminating in belt loop 1e, is preferably constructed of matt finish clear vinyl of approximately 0.025 inches thickness. Such vinyl is readily fabricatable into all structural aspects of the present invention. It supports of making articles which are aseptic and free of foreign contamination. It provides good strength for the required fluid containment and support holding aspects of the present invention. It presents a smooth and nonirritating surface to the skin of the patient. Finally, it provides a smooth and non-porous surface which may be readily cleaned if required.

Finally in FIG. 1, the unitary urine drainage bag and support harness component of the present invention is supported by a belt 4a threading belt loop 1e. The belt is approximately two inches wide and of a soft flexible fabric. The belt has a "hook" Velcro ® fastener 4b of small area at one end, and is otherwise coated over its entire surface with "loop" Velcro ® material. The "hook" Velcro ® fastener 4b is normally but a small square of a few inches dimension which is preliminarily pressed onto one end of the belt. When in use, the belt is circumferentially emplaced around the patient's waist. The "hook" Velcro ® fastener 4b, which may be situated any place along the patient's waist, is affixed by being further pressed to the "loop" Velcro ® at any other point along the surface of the belt 4a. The belt created by this pressed attachment is satisfactorily strong and reliable, and presents no irritation to the waist of the patient. Excess length of the fabric belt material may be tucked within the waistband, or may be severed by scissors and discarded. The belt is generally flexible and soft, having the feel of sp , or foam, rubber.

The "hook" Velcro ® fastener 4b is a connective fastening piece, or tab, which is not normally permanently affixed to the belt, but which is merely stuck onto the one end thereof. Consequently, it may be envisioned that the role of the "hook" and "loop" Velcro ® may be reversed. In such a case the tab would be of "loop" Velcro ® material and the belt would be entirely of "hook" Velcro ® material. However, the more comfortable belt is with the "loop" Velcro ® surface. This is because the "hook" Velcro ® fastening tab is of slight stiffness, as besuits its connective function. It is best made small in order to present no irritating surface nor any sharp edges (including the Velcro ® "hooks" themselves) to the patient.

In aggregate, the belt is very simple and inexpensive. It requires no stitching nor any clasps nor any punched holes nor any appreciable sophistication in construction whatsoever. It is simply a strip of soft fabric, the entire surface of which is "loop" Velcro ® material, which the ends joined to form a belt by a small tab of "hook" Velcro ® material.

In actual application, the entire apparatus shown in FIG. 1 is normally delivered into the locale of patient use already assembled with the belt 4a already threading the unitary urine drainage bag and support harness 1. The apparatus is positioned, the belt loop is closed, and the catheter is summarily attached to the top port 1c. The catheter is then taped to support harness 1b. If desired, further mechanical aids to position and retain the catheter may be employed as desired. When the urine reservoir is full, it can be readily emptied into an appropriate toilet receptacle through the lower vent port 1d without jeopardy of staining or contaminating any porous or non-cleansible parts. Alternatively, the catheter may be summarily disconnected, the upper port 1c may be resealed with a cap, and the entire apparatus may be discarded. During use the apparatus of the invention is non-irritating to the flesh of the patient, and reasonably comfortable and adjustable in support position. Minor soilage of the apparatus is readily cleaned or, if the apparatus becomes contaminated to a degree that it is cost ineffective for medical service personnel to attend to its cleansing or restoration, the entire apparatus may be summarily discarded.

An expanded drawing of the preferred construction of the plastic element of the unitary urine drainage bag and support harness of the present invention is shown in FIG. 2. The representation is not to scale, with the plastic sheet extension 1b, previously seen in FIG. 1, being shortened in length. The urine drainage bag 1a, previously seen in FIG. 1, is comprised of front panel 1a1 and rear panel 1a2, which rear panel 1a2 is but the lower part of plastic sheet 1b. The uppermost port 1c, previously seen in FIG. 1, consists of nozzle 1c1, removable cap 1c2, and bag valve 1c3. Likewise, the bottom port 1c, previously seen in FIG. 1, consists of bottom nozzle 1d1 which can include an integral twist-type low-cost all-plastic valve 1d2. The valve twists under finger pressure to open and shut, respectively allowing draining of urine from the collection bag. In addition to, or in lieu of, the integral valve 1d2 a bottom cap (not shown) similar to removable cap 1c2 may be used. Normally, when the device is received in unused, new, form both top cap 1c2 and any bottom cap are affixed. The top cap 1c2 is removed, and the catheter is attached by slipping it over the top of the nozzle 1c1. If a bottom cap is used, it needs to be removed before draining the valve through nozzle 1d1 and integral valve 1d2.

Also visible in FIG. 2 is the bag valve 1c2. The bag valve 1c2 is of low cost, and serves to establish that the flow of urine through top nozzle 1c2 should be unidirectional from the catheter connected thereto into the urine collection bag. Other types of valves and nozzles known for the control of fluid flow in medical applications may be used. However, simplicity, reliable performance, ease of use, and low cost are paramount goals for implementation of a urine collection system. Consequently, it may be found that the preferred embodiment construction illustrated in FIG. 2 reliably, effectively and efficiently accomplishes the desired function of the collection of urine without the inclusion of further or more expensive features.

In summary, the present invention may be seen to be a urine collection system supportable upon the human torso. The collection system is characterized by simplicity, having only the two parts of a unitary plastic urine drainage bag and integral support harness, plus a fabric belt. Further adaptations of the present invention will be apparent to a fabricator of plastic appliances. For example, the belt loop could be eliminated and a plastic belt could be made out of identical material as is now used for construction of the support harness and urine drainage bag. However, such belt would be less comfortable to the user, would entail a fastening system neither so simple nor so flexible as the Velcro ® closure, and would not be anticipated to be cheaper than the fabric belt chosen. Therefore, the present invention must be considered to be alterable in obvious variations either to be both slightly more, or slightly less, complex in the features incorporated. The appropriate scope of the invention should be assessed by the language of the claims, following, and not in terms solely of the preferred embodiment of the invention as has been taught herein.

What is claimed is:

1. A disposable fluid collection system receiving fluid from a patient via a catheter comprising;
    (a) an elongated generally rectangular unitary sheet of nonporous, substantially inelastic, material having
        (i) a first end portion fashioned into at least one belt loop;
        (ii) an opposite second end portion defining a fluid reservoir having a fluid inlet port and a bottom fluid outlet port; and
        (iii) a central planar portion extending between the fluid reservoir and the at least one belt loop, the central planar portion being longer in the direction from the reservoir to the belt loop than it is wide and having a length sufficient to extend from adjacent the patient's leg to adjacent the patient's hip such that the reservoir may be located adjacent the patient's leg while the at least one belt loop is located adjacent the patient's waist, the central planar portion presenting a substantially smooth surface to which the catheter may readily and repetitively be taped and untaped; and
    (b) a belt disposed through said at least one belt loop of sufficient length so as to circumferentially engage the waist of the patient so that the material sheet hangs at the waist of the patient;
    wherein, the substantially inelastic material employed for the sheet of material and the dimension of the sheet of material cooperate to minimize visible bulging of the system when the system is worn under a patient's clothing.

2. The fluid collection system of claim 1 wherein the belt is made entirely of loop-type material, and is fastened about the waist of the patient by a small patch of hook-type material.

3. The fluid collection system of claim 1 wherein the fluid inlet port contains a one-way valve.

4. The fluid collection system of claim 1 wherein the fluid outlet port contains a valve which blocks fluid flow through the outlet port during collection of fluid within the reservoir, but which can be opened to allow gravity drainage of fluid from the reservoir via the outlet port.

5. The fluid collection system of claim 1 further including a catheter joined to said fluid inlet port for directing fluid from the patient to the reservoir.

6. A method of securing a fluid collection bag to a catheter from a catheterized patient comprising:
    extending a single wall of a fluid collection bag into an elongated sheet extension outside of the reservoir defined by said bag;
    folding at its terminus said elongated sheet extension into a belt loop, said belt loop at sufficient extension from the reservoir of the fluid collection bag so as to permit the fluid collection bag to hang down in the area of the patient's leg while the belt loop is at the patient's waist, said extension being longer in the direction from the reservoir to the belt loop than said extension is wide;
    threading the belt loop with a belt and securing the belt about the patient;
    flow connecting the catheter from the catheterized patient to the reservoir of the fluid collection bag so as to receive fluid from the patient in the reservoir while the reservoir is positioned adjacent the patient's leg such that visible bulging of the fluid collection bag when worn under the patient's clothing is minimized; and
    affixing the catheter to the elongated sheet extension of the single wall of the fluid collection bag by taping it.

7. The fluid collection system as claimed in claim 1, wherein the fluid reservoir defined by the second end portion of the unitary sheet is formed integral with the unitary sheet.

8. The fluid collection system as claimed in claim 1, wherein the fluid reservoir comprises a second sheet of substantially nonporous material, substantially sealed at its periphery with the first sheet and defining a fluid receiving area between the first and second sheets.

9. The fluid collection system as claimed in claim 1, wherein the fluid inlet port is arranged between the second end of the unitary sheet and the central planar portion of the unitary sheet.

10. The fluid collection system as claimed in claim 9, further comprising first securing means for securing the catheter to the fluid inlet port to allow communication of fluid from the patient to the fluid reservoir, and second securing means for securing the catheter periphery to the central planar portion of the unitary sheet.

11. The fluid collection system as claimed in claim 1, further comprising first securing means for securing the catheter to the fluid inlet port to allow communication of fluid from the patient to the fluid reservoir, and second securing means for securing the catheter periphery to the central planar portion of the unitary sheet.

12. A fluid collection system for receiving fluid conveyed from a patient through a fluid conveying tube, the system comprising:
    a belt of sufficient length to fit about the waist of the patient;
    a first sheet of substantially inelastic, nonporous material arrangeable to extend from the belt, the first sheet having a first end adjacent the belt and a second end arrangeable adjacent a leg of the patient upon the belt being fitted about the patient's waist; and a fluid receptacle integral with and made of substantially the same type of material as the first sheet and located between the first and second ends of the first sheet, the fluid receptacle being operatively connectable with the fluid conveying tube;

the first sheet having a sheet portion extending between the fluid receptacle and the belt and being elongated in the direction from the fluid receptacle to the belt, whereby the sheet portion is longer in said direction than it is wide, the sheet portion presenting a surface to which the fluid conveying tube may be readily and repetitively secured and unsecured;

wherein the substantially inelastic material employed for the first sheet and the fluid receptacle and the dimension of the first sheet cooperate to minimize visible bulging of the fluid collection system when the system is worn under the patient's clothing.

13. A fluid collection system as claimed in claim 12, wherein the fluid receptacle is provided with a fluid inlet port located below the sheet portion which extends between the fluid receptacle and the belt.

14. A fluid collection system as claimed in claim 12, wherein the fluid inlet port is provided with a one-way valve arranged to pass fluid into the fluid receptacle.

15. A fluid collection system as claimed in claim 12, wherein the fluid receptacle is provided with a fluid outlet port.

16. A fluid collection system as claimed in claim 15, wherein the fluid outlet port is arranged adjacent the second end of the first sheet.

17. A fluid collection system as claimed in claim 15, wherein the fluid outlet port is provided with a closable valve, closable to substantially prevent the passage of fluid from the fluid receptacle and out of the outlet port.

18. A fluid collection system as claimed in claim 12, wherein the fluid receptacle comprises a second sheet of substantially nonporous material, substantially sealed at its periphery with the first sheet and defining a fluid receiving area between the first and second sheets.

19. A fluid collection system as claimed in claim 18, wherein the second sheet is permanently sealed at its periphery with the first sheet.

20. A fluid collection system as claimed in claim 12, wherein the first end of the first sheet is fashioned into at least one belt loop through which the belt may extend.

21. A fluid collection system as claimed in claim 12, wherein the belt and the first sheet are provided as a unitary structure.

22. A fluid collection system as claimed in claim 12, wherein the belt is provided with loop-type material over substantially its entire length and is further provided with a portion of hook-type material which is securable with the loop-type material.

23. A fluid collection system as claimed in claim 18, wherein the second sheet extends from the second end of the first sheet and terminates at a location on the first sheet between the first and second ends of the first sheet.

24. A fluid collection system as claimed in claim 12, wherein the fluid receptacle is supported by the belt by no more than the first sheet.

25. A fluid collection system as claimed in claim 12, further comprising a second sheet of substantially nonporous material, the second sheet being sealed about its substantially entire periphery to the first sheet at a location on the first sheet between the second end and the portion of the first sheet which extends between the fluid receptacle and the belt.

* * * * *